(12) United States Patent
Moloy et al.

(10) Patent No.: US 8,058,481 B2
(45) Date of Patent: *Nov. 15, 2011

(54) ALKYL ALKOXYLATES CONTAINING UNIQUE END GROUPS

(75) Inventors: Kenneth Gene Moloy, Hockessin, DE (US); James A. Schultz, Swedesboro, NJ (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 176 days.

This patent is subject to a terminal disclaimer.

(21) Appl. No.: 12/432,821

(22) Filed: Apr. 30, 2009

(65) Prior Publication Data

US 2010/0280279 A1    Nov. 4, 2010

(51) Int. Cl.
*C07C 41/03* (2006.01)
*C07C 43/04* (2006.01)
*C07C 67/26* (2006.01)

(52) U.S. Cl. ........ 568/618; 568/608; 568/609; 568/610; 568/614; 568/615; 568/622; 568/625; 568/630; 568/645; 568/650; 568/649; 568/664; 568/669; 568/670; 568/676; 568/677; 560/239; 560/240; 560/254; 560/255; 560/263; 560/265

(58) Field of Classification Search .......... None
See application file for complete search history.

(56) References Cited

U.S. PATENT DOCUMENTS

| | | | |
|---|---|---|---|
| 2,976,307 A | 3/1961 | Rudner et al | |
| 3,007,970 A | 11/1961 | Ashby | |
| 5,026,923 A * | 6/1991 | Kemp | 568/618 |
| 5,608,116 A | 3/1997 | Halling et al. | |
| 6,335,423 B1 | 1/2002 | Varma | |
| 6,352,798 B1 | 3/2002 | Lee et al. | |
| 6,593,500 B2 * | 7/2003 | Priou et al. | 568/618 |
| 2005/0004404 A1 | 1/2005 | Muller et al. | |
| 2005/0256331 A1 | 11/2005 | Der Puy et al. | |
| 2006/0069220 A1 * | 3/2006 | Meurs et al. | 526/160 |

FOREIGN PATENT DOCUMENTS

| | | | |
|---|---|---|---|
| JP | 2-256634 | * | 10/1990 |
| JP | 2004154664 | * | 6/2004 |
| SU | 245070 | * | 6/1969 |
| WO | 9705944 A1 | | 2/1997 |

OTHER PUBLICATIONS

Kwong, Mild and Efficient Copper-Catalyzed Amination of Aryl Bromides with Primary Amines, Organic Letters, Mar. 2003, vol. 5, No. 6, pp. 793-796.*

Inokuma et al., Surface active crown ethers. III. Convenient method for synthesis and catalytic action of thiacrown ethers and alkyl thiacrown ethers, Yukagaku, 1980, vol. 29, No. 10, pp. 767-770, abstract only.*

R. E. Davis et al., Boron Hydrides V. Methanolysis of Sodium Borohydride, J. Am Chem Soc., 1962, V. 84, pp. 895-898, March.

J. H. Golden et al., Disproportionation of Alkoxyborohydrides: A 11B NMR Study of The Reaction Between Sodium Borohydride and Fluorinated Alcohols and Phenols. The Preparation of Tris(Fluoroalkoxy)- and Tris(Fluoropenoxy)Borohydrides, Inorg. Chem., 1992, vol. 31, pp. 1533-1535.

A. G. Campana et al., Sodium Tetramethoxyborate: An Efficient Catalyst for Michael Additions of Stabilized Carbon Nucleophiles, J. Org. Chem., 2007, vol. 72, pp. 8127-8130.

* cited by examiner

Primary Examiner — Rosalynd Keys

(57) ABSTRACT

Described is a process for the alkoxylation of alcohols with I, Cl, or $CH_3CO_2$ endgroups, using alkylene epoxides in the presence of boron based catalysts.

14 Claims, No Drawings

ALKYL ALKOXYLATES CONTAINING UNIQUE END GROUPS

RELATED APPLICATIONS

This application is related to copending Application No. US2010-0280278 and copending Application No. US2010-0279852, filed on the same date as this application.

FIELD OF INVENTION

The present invention is directed to processes for the alkoxylation of alcohols using alkylene epoxides in the presence of boron based catalysts, and to the compounds thus produced.

BACKGROUND

Alcohol alkoxylate containing materials have been used in a wide variety of industrial applications, for example as nonionic surfactants, additives, and conjugates for biologically-active molecules. They are typically prepared by the reaction of an alcohol with an alkylene epoxide such as ethylene oxide (i.e. oxirane) or propylene oxide (i.e. 2-methyoxirane) in the presence of one or more catalysts.

Known catalyst systems and processes for the alkoxylation of alcohols include Lewis acids such as boron trifluoride or silicon tetrafluoride, alone in combination with metal hydrides, fluorides, alkyls or alkoxides. Such acidic materials also catalyze side reactions such as dimerization of alkylene epoxides to form highly undesirable dioxanes during the alkylalkoxylation. For this reason many processes use strongly basic catalysts to alkoxylate alcohols. However, some alcohols are not stable to strong base. For instance, halohydrins, $XCR_2CR_2OH$ (X=halogen), are well known to form epoxides in the presence of base and are used for this purpose synthetically to convert olefins to epoxides.

Alcohol alkoxylates wherein the alcohol group bears a reactive functional group are of interest in several applications. They are useful for the synthesis of new molecules and materials bearing one or more alkoxylate chains such as novel surfactants and metal ligating agents. As another example, the binding of polyethylene glycol (PEG) to biological molecules (peptides, proteins), known as "PEGylation", is used to modify the physical and solution properties of those molecules to enhance their pharmaceutical properties.

Alkoxylates useful for these synthetic reactions are substituted with a functionalized alcohol group at only one end of the alkoxylate chain. However, known methods for the preparation of such mono-alkoxylates involve multistep procedures and require tedious separations. A one-step alkoxylation of an appropriately substituted alcohol would present a significant advance. However, the functional groups commonly used to bind PEGs to other molecules undergo ready reaction with base, especially the strong alkoxide bases required to catalytically alkoxylate alcohols. For a one-step process to be successful the functional group must be unreactive towards the alkoxylation catalyst.

There exists a need therefore for catalysts suitable for the selective alkoxylation of functionalized alcohols

SUMMARY

One aspect of the present invention is a process comprising: contacting one or more alcohols of the formula $R^1$—OH with one or more 1,2 alkylene epoxides of the formula Q(O), wherein Q is a linear alkylene group of the formula $C_yH_{2y}$, where y is an integer from 2 to 10, $R^1$ is Y—R' where R' is a linear, branched, cyclic, or aromatic hydrocarbyl group, optionally substituted, having from 1 to 30 carbon atoms, and Y is I, Br, Cl or $CH_3CO_2$;

at a temperature from about 60° C. to about 200° C. and a pressure from ambient atmospheric pressure to about 1035 KPa;

in the presence of a catalyst at a molar ratio of alcohol to catalyst of from about 200 to 15, wherein the catalyst is $MB(OR^1)_x(X)_{4-x}$ or $B(OR^1)_3/MX$, where M is $Na^+$, $K^+$, $Li^+$, $R^2R^3R^4R^5N^+$, or $R^2R^3R^4R^5P^+$, where $R^2$, $R^3$, $R^4$, and $R^5$ independently are hydrocarbyl groups, and x is 1 to 3;

to form an alkyl alkoxylate of the formula $R^1O(QO)_mH$ where m is from 1 to 20.

Another aspect of the present invention is a compound of the formula $R^1O(QO)_mH$ formed by a process comprising: contacting one or more alcohols of the formula $R^1$—OH with one or more 1,2 alkylene epoxides of the formula Q(O), wherein Q is a linear alkylene group of the formula $C_yH_{2y}$, where y is an integer from 2 to 10, $R^1$ is Y—R' where R' is a linear, branched, cyclic, or aromatic hydrocarbyl group, optionally substituted, having from 1 to 30 carbon atoms, and Y is I, Br, Cl or $CH_3CO_2$;

at a temperature from about 60° C. to about 200° C. and a pressure from ambient atmospheric pressure to about 1035 KPa;

in the presence of a catalyst at a molar ratio of alcohol to catalyst of from about 200 to 15, wherein the catalyst is $MB(OR^1)_x(X)_{4-x}$ or $B(OR^1)_3/MX$, where M is $Na^+$, $K^+$, $Li^+$, $R^2R^3R^4R^5N^+$, or $R^2R^3R^4R^5P^+$, where $R^2$, $R^3$, $R^4$, and $R^5$ independently are hydrocarbyl groups, and x is 1 to 3;

to form an alkyl alkoxylate of the formula $R^1O(QO)_mH$ where m is from 1 to 20.

Another aspect of the present invention is a composition of the formula $R^1O(QO)_mH$ that is a telomeric mixture, wherein Q is a linear alkylene group of the formula $C_yH_{2y}$, where y is from 2 to 10, and $R^1$ is Y—R' where R' is a linear, branched, cyclic, or aromatic hydrocarbyl group, optionally substituted, having from 1 to 30 carbon atoms, Y is I, Br, Cl or $CH_3CO_2$, and m is from 1 to 20.

DETAILED DESCRIPTION

As used herein, the term "hydrocarbyl" means a straight chain, branched or cyclic arrangement of carbon atoms connected by single, double, triple, or aromatic carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, cyclopentyl, methylcyclopentyl, cyclohexyl, methylcyclohexyl, benzyl, phenyl, o-tolyl, m-tolyl, p-tolyl, xylyl, vinyl, allyl, butenyl, cyclohexenyl, cyclooctenyl, cyclooctadienyl, and butynyl.

"Optional" or "optionally" means that the subsequently described event or circumstance may or may not occur, and that the description includes instances where said event or circumstance occurs and instances where it does not. For example, the phrase "optionally substituted" means that moiety may or may not be substituted and that the description includes both unsubstituted moieties and unsubstituted moieties.

When a group or moiety is referred to herein as being "substituted" it means that the group or moiety contains one or more substituent groups that are inert under the process conditions to which the compound containing these groups is subjected (e.g., an inert functional group, see below). The substituent groups can be attached pendant to the original moiety or may replace one or more atoms of the moiety. The substituent groups also do not substantially detrimentally interfere with the process described herein. Included in the meaning of "substituted" are chains or rings containing one or more heteroatoms, such as nitrogen, oxygen and/or sulfur. In a substituted hydrocarbyl, all of the hydrogens may be substituted, as in trifluoromethyl.

By "inert functional group" is meant a group other than hydrocarbyl or substituted hydrocarbyl that is inert under the process conditions to which the compound containing the group is subjected. The functional groups also do not substantially interfere with any process described herein that the compound in which they are present may take part in. Examples of functional groups include halo (fluoro, chloro, bromo and iodo), and ether.

By "alkyl" it is meant a monovalent hydrocarbyl group containing only single bonds.

By "alkylene" it is meant a divalent hydrocarbyl group containing only single bonds.

The present invention provides processes for preparing alkyl alkoxylates, especially functionalized alkoxylates via epoxidation, using a boron-based catalyst. The catalyst can be used with a large variety of alcohols. The alkyl alkoxylates are useful in the synthesis of new molecules and materials bearing one or more alkoxylate chains such as novel surfactants and metal ligating agents.

In one embodiment, the process comprises: contacting one or more alcohols of the formula $R^1$—OH with one or more 1,2 alkylene epoxides of the formula Q(O), wherein Q is a linear alkylene group of the formula $C_yH_{2y}$, where y is an integer from 2 to 10, $R^1$ is Y—R' where R' is a linear, branched, cyclic, or aromatic hydrocarbyl group, optionally substituted, having from 1 to 30 carbon atoms, and Y is I, Br, Cl or $CH_3CO_2$;

at a temperature from about 60° C. to about 200° C. and a pressure from ambient atmospheric pressure to about 1035 KPa;

in the presence of a catalyst at a molar ratio of alcohol to catalyst of from about 200 to 15, wherein the catalyst is $MB(OR^1)_x(X)_{4-x}$ or $B(OR^1)_3$/MX, where M is $Na^+$, $K^+$, $Li^+$, $R^2R^3R^4R^5N^+$, or $R^2R^3R^4R^5P^+$, where $R^2$, $R^3$, $R^4$, and $R^5$ independently are hydrocarbyl groups, and x is 1 to 3;

to form an alkyl alkoxylate of the formula $R^1O(QO)_mH$ where m is from 1 to 20.

$R^1$ is Y—R', where Y is I, Br, Cl or $CH_3CO_2$, typically I or Br.

In one embodiment a mixture of alcohols of the formula $R^1$OH can be contacted with the 1,2-alkylene epoxides in the process, to produce a corresponding mixture of alkyl alkoxylates In another embodiment the process can form a telomeric mixture of alkyl alkoxylates. As used herein, a telomeric mixture is a plurality of telomers whose polymerization degrees m are different from each other. A telomer is formed when a compound (C) is added to a second compound (AB) so that a mixture is formed of polymers of low polymerization degree represented by the formula: $A(C)_mB$, in the range of 1 to 20. Thus, in some embodiments the processes disclosed herein can produce a telomeric mixture of alkyl alkoxylates of the formula $R^1O(QO)_mH$, having different values of m. The processes disclosed herein are particularly suitable for the production of telomers with an average degree of polymerization of 1-20, more typically 6-12, although telomers with higher values of m up to about 1000 are possible.

The 1,2 alkylene epoxide of the formula Q(O) can be ethylene oxide, propylene oxide, 1,2-butylene oxide, 2,3-butylene oxide, and styrene oxide, or a mixture thereof, and typically can be ethylene oxide or propylene oxide.

Catalysts suitable for the processes disclosed herein include $MB(OR^1)_x(X)_{4-x}$ or $B(OR^1)_3$/MX. By $B(OR^1)_3$/MX is meant a two component catalyst which is a mixture of $B(OR^1)_3$ and MX. The two components can be added separately, in any order, or simultaneously, to the process. $R^1$ is as defined above. In the formula $MB(OR^1)_x(X)_{4-x}$ x can be 1 to 3 but is typically 3.

M is a cation of the alkali metals $Na^+$, $K^+$, $Li^+$ or a cation of the type $R^2R^3R^4R^5N^+$ or $R^2R^3R^4R^5P^+$ where $R^2$, $R^3$, $R^4$, and $R^5$ independently are hydrocarbyl groups of 1 to 20 carbon atoms, and are the same or different. Typically, $R^2$, $R^3$, $R^4$, and $R^5$ independently are alkyl groups of from 1 to 4 carbons, such as butyl, and can be the same or different. In one embodiment, M is $R^2R^3R^4R^5N^+$.

X is fluoride, bromide, or iodide, but is typically I.

The catalysts can be obtained commercially or prepared by any method known in the art, such as the methods disclosed herein below In one embodiment, the process includes contacting an alcohol with an alkylene oxide in the presence of a catalyst. The alcohol and catalyst can be contacted with the alkylene oxide either simultaneously or in any order. Typically the catalyst is either added to, or generated in, the neat alcohol, which also serves as a solvent for the reaction. One or more co-solvents may be additionally used, provided that the solvent or solvents are substantially inert to all reagents and products. When the desired product is of high enough molecular weight to become solid, such as when m is greater than about 100, then a solvent is desired. The catalyst and alcohol reaction mixture is then treated with the alkylene oxide at elevated temperature until the desired conversion is achieved.

The catalyst is used in an amount relative to the alcohol of from about 0.1 mole % to about 11 mole %, typically about 0.5% to about 8%, more typically about 1 mole % to about 6%. The alkylene oxide is typically fed to the catalyst/alcohol solution as a liquid or vapor after the addition of the catalyst and alcohol. The amount of alkylene oxide added to the reaction mixture is not critical other than providing the minimum amount necessary to provide the desired number of alkyloxy units in the final product.

The amount of alkylene oxide used is variable, and is determined by the physical properties desired in the alkoxylated alcohol product. Thus, in some cases the average number of alkoxy groups per starting alcohol may need to be relatively low, e.g., 2 to 6, while for other cases a significantly higher number may be required such as from 8 to 30 or more.

The alkylene oxide can be added to the reaction before heating or after the reactor and alcohol/catalyst solution has reached the desired reaction temperature. The alkylene oxide can be added at once, batchwise, or by continuous feed.

The process is typically performed under inert atmosphere, such as nitrogen or another inert gas, for safety reasons owing to the flammability of many alkylene oxides. It is typical to run the process under anhydrous conditions since water will usually be alkoxylated, thereby producing contaminants. Water may also inhibit or poison some catalysts.

The reaction temperature is variable and can range from about 60° C. to about 180° C., and preferably is from about 80° C. to 140° C. The desired temperature is primarily determined by the reaction times that can be tolerated, lower temperatures giving longer reaction times, and higher temperatures giving shorter reaction times.

The reaction is run at the pressure generated during the reaction, generally about 0 to about 200 psig, typically about 0 to about 100 psig.

Agitation is not required, but is usually provided to facilitate a homogeneous mix and to facilitate heat transfer.

The alkyl alkoxylates and telomeric mixtures produced by the processes disclosed herein can have any desired number of alkyloxy units, allowing the tailoring of properties for the desired end use. The alkyloxy units will typically be present at about 10% to about 90% by weight of the alkyl alkoxylate composition; more typically about 20% to about 70%.

The compounds $MB(OR)_x(X)_{4-x}$ where x is from 1 to 3 can be prepared by combination of the neutral borate esters $B(OR)_3$ with $M^+X^-$. The $B(OR)_3$ can be formed in a first step followed by the addition of MX in a second step. Alternatively, $MB(OR)_x(X)_{4-x}$ can be generated in a single step by combination of MX and either $B(OH)_3$ or $B_2O_3$ in the alcohol ROH and then optionally removing water.

$B(OR)_3$ can be prepared by reaction of $B(OH)_3$ or $B_2O_3$ and HOR with elimination of water. Alternatively, they can be prepared from a boron halide such as $BCl_3$ and an alcohol with the formation of HCl. The HCl generated is removed with a base. The $B(OR)_3$ compounds can be prepared independently or generated in the same reactor in which the alkoxylation is to be performed. Water removal is optional but is typically performed to avoid the formation of poly(alkylene glycols), which are formed by the alkoxylation of water. If the presence of poly(alkylene glycols) in the alcohol alkoxylate product is unacceptable, then water should be removed prior to performing the alkoxylation reaction.

EXAMPLES

The following abbreviations were used: "L" means liter, "mol" means mole, "mL" means milliliter, "%" means percent, "ca." means approximately, "g" means gram, "h" means hour, "EO" means ethylene oxide.

All $B(OR)_3$ compounds were prepared by previously published methods such as that described in Cotton, F. A.; Wilkinson, G. "Advanced Inorganic Chemistry, Fifth Edition", Wiley-Interscience: New York, 1988, p 168 and p 171. Malkowsky, et al., Eur. J. Inorg. Chem. 2006, 1690 where a oxyboron species such as $B(OH)_3$ or $B_2O_3$ are reacted with the appropriate alcohol. The reactions proceeded rapidly in a solvent, typically refluxing toluene. Water was removed continuously by standard methods to ensure complete conversion of the oxyboron material to the ester $B(OR)_3$. These compounds were characterized by multinuclear NMR (1H, 13C, 19F), mass spectrometry, and elemental analysis. The following is a representative reaction.

Example 1

Boric acid (7.64 mmol) and 2-iodoethanol (23.7 mmol) were refluxed in 25 mL of toluene and constant water removal using a Dean-Stark trap. When water removal was complete the toluene was removed under vacuum to yield 3.15 g of light amber liquid (79%).

$^1$H NMR (CDCl$_3$): 4.06 (t, 2H), 3.30 (t, 2H).
$^{13}$C NMR (CDCl$_3$): δ4.1, 5.6.

Example 2

Boric acid (0.646 g, 0.0205 mol) and 2-bromoethanol (4.05 g, 0.0324 mol) were refluxed in 25 mL of toluene and constant water removal using a Dean-Stark trap. When water removal was complete the toluene was removed under vacuum to yield 2.16 g of a light brown liquid (54%).

1H NMR (CDCl$_3$): 4.05 (t, 2H), 3.41 (t, 2H).
13C NMR (CDCl$_3$): 62.45, 31.47.

Example 3

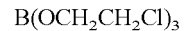

Boric acid (0.992 g, 0.016 mol) and 2-chloroethanol (4.00 g, 0.0497 mol) were refluxed in 25 mL of toluene and constant water removal using a Dean-Stark trap. When water removal was complete the toluene was removed under vacuum to yield 2.34 g of a light brown liquid (59%).

1H NMR (CDCl$_3$): 4.00 (t, 2H), 3.54 (t, 2H).
13C NMR (CDCl$_3$): δ2.7, 43.4.

Example 4

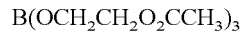

A flask was charged with boric acid (0.773 g, 0.0125 mol) and 2-hydroxyethyl acetate (4.03 g, 0.0387 mol) in 25 mL of toluene. The mixture was refluxed for 24 h with water removal. The solution was cooled to room temperature and the toluene was removed on a rotary evaporator. The light yellow, viscous liquid was dried thoroughly under high vacuum.

1H NMR (CDCl$_3$): 4.25 (t, 2H), 4.17 (t, 2H), 2.08 (s, 3H).
13C NMR (CDCl$_3$): 171.0, 64.1, 62.4, 20.8.

Comparative Example A

A vial was charged with 1.0 g (5.8 mmol) of 2-iodoethanol, a stir bar, and a thermocouple. Powdered KOH (0.18 g, 0.32 mmol, 5.5 mol %) was added. Immediate reaction occurred as indicated by a temperature rise of 4-5° C. An aliquot was dissolved in deuterated methanol and analyzed by 1H and $^{13}$C NMR, which showed the formation of ethylene oxide in 82% yield and ethylene glycol in 15% yield based on the limiting reagent (KOH).

This example demonstrates that 2-iodoethanol reacts instantly at room temperature with a typical alkoxylation catalyst (KOH) to cleave the carbon-iodine bond and form a mixture of the epoxide and the glycol.

Example 5

Ethoxylation of 2-iodoethanol

A reactor was charged with 2-iodoethanol (1.72 g, 0.01 mol), Bu$_4$NI (0.148 g, 0.4 mmol), and B(OCH$_2$CH$_2$I)$_3$ (0.209 g, 0.4 mmol). Ethylene oxide (5.0 mL, 0.10 mol) was added and the reactor was then heated to 100° C. Upon reaching 95-100° C. rapid pressure drop was noticeable. After a few hours the pressure dropped to 0 psig. The reactor was cooled and any unreacted ethylene oxide was removed under vacuum. 5.76 g of a light yellow liquid was recovered.

GC analysis showed less than 2% unreacted 2-iodoethanol. LCMS (positive electrospray, individual components identified as $(M^+H)^+$ and $(M^+Na)^+$ ions) confirmed the identity of the product as a distribution of ethoxylates of 2-iodoethanol, $ICH_2CH_2O(CH_2CH_2O)_nH$ where n=1 to ca. 30 and peaking at n=8-9.

1H NMR (CD$_3$OD): 3.83 (t, 2 H, ICH$_2$CH$_2$O$^-$), 3.75-3.71 (m, 34 H, —OCH$_2$CH$_2$O$^-$), 3.65 (t, 2H, CH$_2$CH$_2$OH), 3.40 (t, 2 H, ICH$_2$CH$_2$O$^-$). Integration gave an average value for n of 8.5.

Example 6

Ethoxylation of 2-iodoethanol

A reactor was charged with 2-iodoethanol (1.72 g, 0.01 mol), Bu$_4$NI (0.148 g, 0.4 mmol), and B(OCH$_2$CH$_2$I)$_3$ (0.209 g, 0.4 mmol). Ethylene oxide (7.0 mL, 0.14 mol) was added and the reactor was then heated to 100 C. Upon reaching 95-100° C. rapid pressure drop was noticeable. After a few hours the pressure dropped to 0 psig. The reactor was cooled and any unreacted ethylene oxide was removed under vacuum. 7.00 g of a colorless, waxy solid was recovered.

Analysis by GC and LCMS confirmed the product is the ethoxylate of 2-iodoethanol, ICH$_2$CH$_2$—O—(CH$_2$CH$_2$O)$_n$H with n ranging from 1 to 30.

1H NMR (CD$_3$OD) confirmed the product identity and gave an average value for n of ca. 11.5

Example 7

Ethoxylation of 2-iodoethanol

A reactor was charged with 2-iodoethanol (2.8 g, 0.016 mol), Bu$_4$NI (0.016 g, 0.4 mmol), and B(OCH$_2$CH$_2$I)$_3$ (0.085 g, 0.16 mmol). Ethylene oxide (5 mL, 0.1 mol) was added and the reactor was then heated to 100° C. Upon reaching 95-100° C. rapid pressure drop was noticeable. After a few hours the pressure dropped to 0 psig. The reactor was cooled and any unreacted ethylene oxide was removed under vacuum. 6.80 g of a pale yellow liquid was recovered.

GC analysis showed 99.3% conversion of 2-iodoethanol. LCMS confirmed the product is a mixture of 2-iodoethanol ethoxylates, ICH$_2$CH$_2$O(CH$_2$CH$_2$O)$_n$H, where n ranges from 1-15 and peaks at n=5.

1H NMR (CDCl$_3$) confirmed the product identity and integration gave an average value for n of 6.

Example 8

Ethoxylation of 2-chloroethanol

A reactor was charged with 2-chloroethanol (0.805 g, 0.01 mol), Bu$_4$NI (0.148 g, 0.4 mmol), and B(OCH$_2$CH$_2$Cl)$_3$ (0.0997 g, 0.4 mmol). Ethylene oxide (ca. 5 mL, 0.1 mol) was added and the reactor was then heated to 100° C. and the pressure rose to 125 psig. After stirring overnight the pressure dropped to 0 psig, indicating complete ethylene oxide consumption. The reactor was cooled and 5.19 of ethoxylate product was collected.

Product identity was confirmed by NMR and LCMS.

1H NMR (CD$_3$Cl): 3.76 (t, 2 H, ClCH$_2$CH$_2$O$^-$), 3.74-3.59 (m, 55 H). Integration gave an average value for n of 11.9.

Example 9

Ethoxylation of 2-bromoethanol, Iodide Promoter

A reactor was charged with 2-bromoethanol (4.0 g, 0.032 mol), Bu$_4$NI (0.473 g, 1.28 mmol), and B(OCH$_2$CH$_2$Br)$_3$ (0.49 g, 1.28 mmol). Ethylene oxide (ca. 5 mL, 0.1 mol) was added and the reactor was then heated to 100° C. and the pressure rose to 60 psig. After stirring overnight the pressure dropped to 0 psig, indicating complete ethylene oxide consumption. The reactor was cooled and 8.01 g of ethoxylate product was collected. GC and LCMS showed the ethoxylate was a mixture of the desired Br(CH$_2$CH$_2$O)$_n$H and small amounts of the halogen substitution product I(CH$_2$CH$_2$O)$_n$H.

Example 10

Ethoxylation of 2-bromoethanol, Bromide Promoter

A reactor was charged with 2-bromoethanol (1.25 g, 0.01 mol), KBr (0.0476 g, 0.4 mmol), and B(OCH$_2$CH$_2$Br)$_3$ (0.153 g, 0.4 mmol). Ethylene oxide (ca. 5 mL, 0.1 mol) was added and the reactor was then heated to 100° C. and the pressure rose to a maximum of 130 psig. After reacting overnight the pressure dropped to 0 psig indicating complete ethylene oxide consumption. After cooling to room temperature 5.79 g of ethoxylate was isolated as a clear, golden yellow liquid. GC showed 96.4% conversion of the starting alcohol. LCMS confirmed the composition of the product as a mixture of Br(CH$_2$CH$_2$O)$_n$H oligomers with n ranging from 1 to about 25 and peaking at 10.

1H NMR (CD$_3$Cl): 3.81 (t, 2 H, BrCH$_2$CH$_2$O$^-$), 3.75-3.60 (m, 36 H), 3.47 (t, 2 H, BrCH$_2$CH$_2$O$^-$). Integration gave an average value for n of 8.0.

Example 11

Ethoxylation of 2-hydroxyethyl Acetate

A reactor was charged with CH$_3$CO$_2$CH$_2$CH$_2$OH (1.04 g, 0.01 mol), Bu$_4$NI (0.0476 g, 0.4 mmol), and B(OCH$_2$CH$_2$O$_2$CCH$_3$)$_3$. Ethylene oxide (ca. 5 mL, 0.1 mol) was added and the reactor was then heated to 110° C. The pressure rose to a maximum value of 105 psig. After stirring overnight the pressure dropped to 0 psig. After cooling to room temperature 5.10 g of the ethoxylate was isolated as an off-white waxy solid. GC showed 94% conversion of starting alcohol. LCMS confirmed the identity of the ethoxylate as a mixture of CH$_3$CO$_2$(CH$_2$CH$_2$)$_n$OH oligomers. Small amounts of I(CH$_2$CH$_2$O)$_n$H were detected by LCMS.

1H NMR (CD$_3$Cl): 4.22 (t, 2 H, CH$_3$CO$_2$CH$_2$CH$_2$O$^-$), 3.75-3.71 (m, 38 H, —OCH$_2$CH$_2$O$^-$), 3.70 (t, 2H, CH$_2$CH$_2$OH), 3.61 (t, 2 H, CH$_3$CO$_2$CH$_2$CH$_2$O$^-$), 2.08 (s, 3H, CH$_3$CO$_2$CH$_2$—). Integration gave an average value for n of 9.0.

What is claimed is:

1. A process comprising: contacting one or more alcohols of the formula R$^1$—OH with one or more 1,2 alkylene epoxides of the formula Q(O), wherein Q is a linear alkylene group of the formula C$_y$H$_{2y}$, where y is an integer from 2 to 10, R$^1$ is Y—R' where R' is a linear, branched, cyclic, or aromatic hydrocarbyl group, optionally substituted, having from 1 to 30 carbon atoms, and Y is I, Br, Cl or CH$_3$CO$_2$;

at a temperature from about 60° C. to about 200° C. and a pressure from ambient atmospheric pressure to about 1035 KPa;

in the presence of a catalyst at a molar ratio of alcohol to catalyst of from about 200 to 15, wherein the catalyst is MB(OR$^1$)$_x$(X)$_{4-x}$ or B(OR$^1$)$_3$/MX, where M is Na$^+$, K$^+$, Li$^+$, R$^2$R$^3$R$^4$R$^5$N$^+$, or R$^2$R$^3$R$^4$R$^5$P$^+$, where R$^2$, R$^3$, R$^4$, and R$^5$ independently are hydrocarbyl groups, X is Br, F, or I, and x is 1 to 3;

to form an alkyl alkoxylate of the formula $R^1O(QO)_mH$ where m is from 1 to 20.

2. The process of claim 1 wherein the alkylene epoxide is ethylene oxide, propylene oxide, butylene oxide, or a mixture thereof.

3. The process of claim 1 wherein the alkylene epoxide is ethylene oxide.

4. The process of claim 1 wherein the catalyst is formed in situ.

5. The process of claim 1 where M is $R^2R^3R^4R^5N^+$ and $R^2$, $R^3$, $R^4$, and $R^5$ are alkyl groups of 1 to 4 carbon atoms.

6. The process of claim 1 wherein R' is a alkyl group having from 2-10 carbons.

7. The process of claim 1 wherein R' is $CH_2CH_2$.

8. The process of claim 1 wherein the alkyl alkoxylate of the formula $R^1O(QO)_mH$ is a telomeric mixture.

9. The process of claim 8 wherein the average value of m is from about 6 to about 12.

10. A composition of the formula $R^1O(QO)_mH$ that is a telomeric mixture, wherein
   Q is a linear alkylene group of the formula $C_yH_{2y}$, where y is from 2 to 10, and
   $R^1$ is Y—R' where R' is a linear, branched, cyclic, or aromatic hydrocarbyl group, optionally substituted, having from 1 to 30 carbon atoms, Y is I, Br, Cl or $CH_3CO_2$, and m is from 1 to 20.

11. The composition of claim 10 wherein Y is I or Br.

12. The composition of claim 10 wherein R' is a alkyl group having from 2-10 carbons.

13. The composition of claim 10 wherein R' is $CH_2CH_2$.

14. The composition of claim 13 wherein the average value of m is from about 6 to about 12.

* * * * *